(12) United States Patent
Marissal et al.

(10) Patent No.: US 9,175,120 B2
(45) Date of Patent: Nov. 3, 2015

(54) POLYMERISATION PROCESS

(71) Applicant: Ineos Europe AG, Vaud (CH)

(72) Inventors: Daniel Marissal, Casteau (BE); Philip Van Breuseghem, Temse (BE); Brent R. Walworth, Sint-Niklaas (BE)

(73) Assignee: INEOS EUROPE AG, Vaud (CH)

( * ) Notice: Subject to any disclaimer, the term of this patent is extended or adjusted under 35 U.S.C. 154(b) by 0 days.

(21) Appl. No.: 14/382,185

(22) PCT Filed: Mar. 7, 2013

(86) PCT No.: PCT/EP2013/054650
§ 371 (c)(1),
(2) Date: Aug. 29, 2014

(87) PCT Pub. No.: WO2013/135565
PCT Pub. Date: Sep. 19, 2013

(65) Prior Publication Data
US 2015/0025203 A1  Jan. 22, 2015

(30) Foreign Application Priority Data

Mar. 16, 2012  (EP) .................................... 12159940
Mar. 16, 2012  (EP) .................................... 12159942
Mar. 16, 2012  (EP) .................................... 12159944

(51) Int. Cl.
*C08F 2/06*      (2006.01)
*C08F 2/38*      (2006.01)
*C07C 7/00*      (2006.01)
*C08F 210/16*    (2006.01)
*C08F 2/01*      (2006.01)
*C08F 6/00*      (2006.01)
*C08F 210/14*    (2006.01)

(52) U.S. Cl.
CPC ................. *C08F 210/16* (2013.01); *C07C 7/00* (2013.01); *C08F 2/01* (2013.01); *C08F 2/06* (2013.01); *C08F 6/001* (2013.01)

(58) Field of Classification Search
CPC .............. C08F 2/01; C08F 6/001; C07C 7/00
USPC ................................................... 526/905, 65
See application file for complete search history.

(56) References Cited

U.S. PATENT DOCUMENTS

| 3,152,872 | A | 10/1964 | Scoggin et al. |
| 3,842,060 | A | 10/1974 | McDonald et al. |
| 4,182,810 | A | 1/1980 | Willcox |
| 4,215,207 | A | 7/1980 | Durand et al. |
| 4,424,341 | A | 1/1984 | Hanson et al. |
| 4,589,957 | A | 5/1986 | Sherk et al. |
| 6,042,790 | A | 3/2000 | Hottovy et al. |
| 6,262,191 | B1 | 7/2001 | Hottovy et al. |
| 2003/0191251 | A1 | 10/2003 | McGrath |
| 2007/0142576 | A1 | 6/2007 | Tait et al. |
| 2010/0305283 | A1* | 12/2010 | Dorini et al. .................... 526/64 |

FOREIGN PATENT DOCUMENTS

| EP | 2 336 200 A1 | 6/2011 |
| EP | 2 336 201 A1 | 6/2011 |
| WO | WO 94/28032 A1 | 12/1994 |
| WO | WO 99/60028 A2 | 11/1999 |
| WO | WO 00/42077 A1 | 7/2000 |
| WO | WO 00/53306 A1 | 9/2000 |
| WO | WO 2004/039847 A1 | 5/2004 |
| WO | WO 2005/003188 A1 | 1/2005 |
| WO | WO 2006/015807 A1 | 2/2006 |
| WO | WO 2009/070261 A2 | 6/2009 |
| WO | WO 2009/070261 A3 | 6/2009 |
| WO | WO 2009/070261 A8 | 6/2009 |
| WO | WO 2011/076371 A1 | 6/2011 |

OTHER PUBLICATIONS

Specification of Co-pending National Phase U.S. Appl. No. 14/382,114, filed Aug. 29, 2014; PCT Int'l Application No. PCT/EP2013/054645, WO 2013/135563 A1, filed Sep. 19, 2013; 21 pgs.
Specification of Co-pending National Phase U.S. Appl. No. 14/382,147, filed Aug. 29, 2014; PCT Int'l Application No. PCT/EP2013/054649, WO 2013/135564 A1, filed Sep. 19, 2013; 22 pgs.

* cited by examiner

*Primary Examiner* — Fred M Teskin
(74) *Attorney, Agent, or Firm* — Nixon & Vanderhye P.C.

(57) ABSTRACT

Polymerization of olefins in a reactor system having two reactors in series, more particularly a process for the polymerization of monomer in at least first and second reactors operated in series. The process includes contacting a first stream containing vapor derived from the effluent withdrawn from the second reactor with a feed stream to the second reactor, the feed stream containing effluent derived from the first reactor.

16 Claims, No Drawings

POLYMERISATION PROCESS

This application is the U.S. national phase of International Application No. PCT/EP2013/054650 filed Mar. 7, 2013 which designated the U.S. and claims priority to European Patent Application Nos. 12159940.1, filed Mar. 16, 2012, Ser. No. 12/159,942.7, filed Mar. 16, 2012 and 12159944.3, filed Mar. 16, 2012, the entire contents of each of which are hereby incorporated by reference.

The present invention relates to a polymerisation process, and in particular to the polymerisation of olefins in a reactor system comprising two reactors in series.

BACKGROUND OF THE INVENTION

The production of polymer powder by polymerisation reactions of monomers in the presence of catalysts is well-known. For example, processes are known and widely operated commercially using both fluidised bed reactors and slurry phase reactors.

In a slurry polymerisation process the polymerisation is conducted in a stirred tank or, preferably, a continuous loop reactor in which a slurry of polymer particles in a liquid medium comprising hydrocarbon diluent is circulated. During the course of polymerisation, fresh polymer is generated by the catalytic polymerisation of monomer and polymer product is removed from the reactor by removing a portion of the slurry.

In a single reactor system the slurry withdrawn from the reactor is treated to separate the polymer particles from the hydrocarbon diluent and other components, such as unreacted monomers, which it is generally desired are recycled to the reactor.

The process where polymer is formed in two reactors in series is also known. The separate reactors can be operated to produce the same product in each reactor, but are most advantageously operated to produce different products in each reactor, in particular to make bimodal polymer products.

In such a process, polymer is produced in the first reactor, withdrawn in the form of a slurry and passed to a second reactor where further production of polymer takes place. Polymer slurry withdrawn from the subsequent reactor is treated to separate the polymer solids from diluent and unreacted reactants, which it is generally desired to recycle to the process.

In a typical separations process, which is also generally used for single reactor systems, withdrawn slurry is heated and passed to a first separation step in which the majority of the diluent and unreacted monomers and comonomers are separated from the polymer solids as a gas (flash gas) at relatively high pressure such that the gas can be condensed without compression and recycled. This is commonly referred to as a "flash step".

Remaining solids and residual diluent are then sent to a second separation step, which may be a further flash tank or may be a flush column where the solids are contacted with a flush gas, such as nitrogen, to remove residual diluent, monomers and comonomers. The second separation step is usually at a lower pressure, and diluent, unreacted monomer and any comonomer separated in the second separator need to be separated from any flush gas, and usually need to be compressed prior to recycle.

Thus, the overall polymerisation process generally includes both high pressure and low pressure recovery systems for recovery and recycle of diluent, monomers and comonomers.

The polymer solids may be taken to further processing, such as blending or pelleting, or to storage.

WO 2006/015807 discloses a polymerisation process in which the gas stream recovered from flashing diluent and unreacted monomer from a slurry of polymer solids is passed to a fractionator. The application of the fractionator to a process comprising two polymerisation loop reactors operated in series is also described. In particular with respect to FIG. 3 there is described a process where the fractionator is used to treat both the flash gas from the second reactor in series and also gas separated from the effluent between the two reactors.

DESCRIPTION OF THE INVENTION

We have now found an improved process for the operation of a polymerisation reactor where gas recovered from the effluent exiting a reactor is contacted with a feed stream to the same reactor.

Thus, in a first aspect the present invention provides a process for the polymerisation of monomer in at least first and second reactors operated in series, which process comprises contacting a first stream comprising vapour derived from the effluent withdrawn from the second or a subsequent reactor with a feed stream to the second reactor, said feed stream comprising effluent derived from the first reactor.

The contacting can take place in any suitable contacting vessel.

The feed stream is generally in a liquid form, and most preferably is a slurry of polymer solids in a liquid medium from the first reactor.

The first reactor is generally the previous reactor in the series to the second reactor.

The first stream comprises vapour derived from the effluent withdrawn from the second reactor or a subsequent reactor. The "subsequent reactor" option can apply where there are 3 or more reactors present in series, at least one of these being subsequent to the second reactor.

For example, three reactors present in a series may be considered as reactors "A", "B" and "C". The present invention may be applied by contacting a feed stream to reactor B, which comprises effluent from reactor A, and the first stream may comprise vapour derived from the effluent withdrawn from reactor B or may comprise vapour derived from the effluent withdrawn from reactor C (or both).

Alternatively, or additionally, the present invention may be applied in such a three reactor series between reactors B and C by contacting a feed stream to reactor C, which comprises effluent from reactor B, with a first stream comprising vapour derived from the effluent withdrawn from reactor C (i.e. in this option reactor B may be considered as the "first reactor" and reactor C as the "second reactor" of the present invention.)

Preferably, the feed stream to the second reactor is contacted with a first stream comprising vapour derived from the effluent withdrawn from the second reactor, and the present invention will hereinafter be illustrated with respect to this option, although it will be equally clear that the process could be equally applied with a first stream derived from a subsequent reactor where one is present.

As an example, a slurry polymerisation process produces an effluent from a second reactor in the form of a slurry of polymer solids in a liquid medium comprising diluent. This stream is usually treated to vaporise the components of the liquid medium, which are then separated from the polymer solids. The first stream is preferably at least a portion of this separated stream, more preferably a majority of, yet more preferably at least 80% by weight of, and most preferably essentially all of, this separated stream.

It is preferred that the first stream is passed from its source, for example a flash tank or other means to separate vaporised medium from the polymer solids/rest of the effluent, to the contacting step without any compression.

It is generally preferred that a majority of, yet more preferably at least 80% by weight of, and most preferably essentially all of the first stream is in vapour form when brought into contact with the feedstream in this first aspect.

In particular, the heat applied to vaporise the liquid medium in the effluent withdrawn from the second reactor and which is therefore present as heat in the first stream can be efficiently utilised to minimise or avoid any additional heat input requirement in the contactor. In contrast, if the first stream is cooled significantly prior to the contactor, as would be required for significant amounts of vapour to condense, then some of that useable heat is lost. In some circumstances it may then be necessary to apply additional heat in the contactor or to the feed stream. It is therefore preferred that cooling of the first stream prior to entry into the contactor is avoided or at least minimised.

More preferably, the first stream is passed directly from its source, for example a flash tank or other means to separate vaporised medium from the polymer solids/rest of the effluent, to the contacting step with the feed stream to the second reactor. By "directly" is meant without intermediate treatment, such as direct or indirect cooling or treatment to separate certain components, such as fines.

In a second aspect, the present invention provides a process for the polymerisation of monomer in a reactor, which process comprises contacting a first stream comprising vapour derived from the effluent withdrawn from the reactor with a feed stream to the reactor, said first stream comprising a majority of the vaporised components of the liquid medium in the effluent withdrawn from the reactor and at least 80% by weight of the first stream is in vapour form when brought into contact with the feed stream.

The feed stream in this second aspect may be any stream comprising one or more components to be fed to the reactor. The feed stream is generally in a liquid form. Most preferably the feed stream in this second aspect comprises effluent derived from a previous reactor in series, in which case this second aspect is a preferred embodiment of the first aspect.

More generally, and whilst it is preferred that cooling of the first stream prior to entry into the contactor is avoided or at least minimised in the first and second aspects, nevertheless, a portion of the first stream may condense prior to contact with the feedstream. It is also possible that the first stream can contain small quantities of solids. For example, whilst the vaporised diluent should be separated from the bulk of the polymer solids prior to being used as the first stream, it is possible that the vapour can contain entrained solids, generally referred to as "fines". A particular advantage of the present invention is that these entrained solids do not need to be removed from the vaporised diluent/first stream prior to the contacting of the first stream with the feed stream to the second reactor, as is described further below.

The pressure at which the first stream is separated from the polymer withdrawn from the second reactor is preferably equal to or higher than the pressure at which it is brought into contact with the feedstream to the second reactor. Thus, the stream may be passed to the contacting step without compression.

By the process of the present invention at least part of the first stream may be recycled to the second reactor without compression and/or at least part of the first stream may be recycled to the second reactor without indirect cooling.

"Indirect cooling" as used herein means use of a cooling medium where the medium to be cooled and the cooling medium do not physically mix. As used herein "indirect cooling" requires the deliberate use of a cooling medium and excludes more general loss of heat to the surroundings from pipework and other equipment. Pipework and equipment may be lagged to reduce such heat losses.

Usually indirect cooling is applied using a cooling medium through the walls of a pipe or vessel, such as in a heat exchanger. At least part of the first stream is preferably recycled to the second reactor as a liquid without any compression or indirect cooling.

More particularly, at least 10 wt % of the first stream passed to the contacting step can be recycled to the second reactor in the post-contacted feedstream to the second reactor. This is described further below.

The first stream is preferably separated from the polymer withdrawn from the second reactor at high pressure, typically between 0.7 MPa and 1.5 MPa, and preferably between 0.8 MPa and 1.2 MPa. The first stream is preferably brought into contact with the feedstream to the second reactor at high pressure, typically between 0.7 MPa and 1.5 MPa, and preferably between 0.8 MPa and 1.2 MPa. Preferably, the pressure at which the first stream is brought into contact with the feedstream to the second reactor is approximately the same as the pressure at which the first stream is separated from the polymer withdrawn from the second reactor. However, a small pressure differential is usually present due to inherent pressure drops in the connecting pipework.

The contacting generally results in post-contacted vapour and a post-contacted feedstream, the vapour being passed to further processing and the feedstream being passed to the reactor.

Generally, the present invention provides a process for the polymerisation of monomer in at least two reactors operated in series, which process comprises contacting the first stream comprising vapour derived from the effluent withdrawn from the second reactor with the feed stream to the second reactor to produce a second stream comprising vapour which is passed to further processing and a third stream which is passed to the second reactor.

As with the feed stream, the third stream is generally in a liquid form and more preferably comprises a slurry of polymer solids in a liquid medium.

The monomer in the process of the present invention is preferably an olefin monomer. For avoidance of any doubt, the term "monomer" as used herein refers to the olefin which is present in the largest amount in the formed polymer, and may also be referred to as the "principal monomer", whilst the term "comonomer" as used herein refers to olefins other than the monomer which may be present. More than one comonomer may be present.

The monomer is preferably ethylene or propylene, most preferably ethylene. Where ethylene is the monomer, propylene may be the comonomer, but the comonomer is preferably selected from 1-butene, 1-hexene and 1-octene, with 1-hexene being most preferred.

Where propylene is the monomer, the comonomer is preferably selected from ethylene, 1-butene, 1-hexene and 1-octene.

The comonomer is preferably 1-hexene.

Preferred diluents which may be used are inert hydrocarbons, more preferably butanes, especially iso-butane, pentanes and mixtures thereof. Iso-butane is most preferred.

The present invention may be applied to a process for the polymerisation of monomer in two reactors connected in series.

Most preferably, the at least two reactors are slurry loop polymerisation reactors which produce effluents comprising a slurry of polymer solids ("polymer slurry"). In this embodiment, a polymer slurry is withdrawn as an effluent from the second reactor, and the first stream is derived from the effluent by flashing all or a portion of the liquid medium to form a vapour, separating this from the polymer solids, and using at least a portion of the separated vapour as the first stream as noted previously.

The polymer slurry withdrawn from the first reactor and contacted with the first stream generally comprises solid polymer and a liquid medium comprising diluent and unreacted monomer. The first stream derived from the effluent withdrawn from the second reactor generally comprises diluent and monomer, and may also comprise comonomers, hydrogen and impurities, such as alkanes and nitrogen.

In more detail, the present invention provides, as a third aspect, a process for the polymerisation of monomer in two slurry loop reactors connected in series, which process comprises:
1) Polymerising in a first loop reactor, monomer in the presence of a diluent to produce a first polymer slurry comprising polymer solids suspended in a liquid medium comprising diluent and unreacted monomer,
2) Withdrawing a portion of the first polymer slurry as a first effluent comprising solid polymer, diluent and unreacted monomer, and passing said first effluent to a contactor to form a second effluent comprising solid polymer, diluent and unreacted monomer,
3) Passing said second effluent to a second loop reactor,
4) Polymerising in the second loop reactor, monomer in the presence of said second effluent, to produce a second polymer slurry comprising polymer solids suspended in a liquid medium comprising diluent and unreacted monomer,
5) Withdrawing a portion of the second polymer slurry as a third effluent comprising solid polymer, diluent and unreacted monomer, and
6) Passing said third effluent to a separation step for separating a first stream comprising vaporised diluent and unreacted monomer from said polymer solids, characterised in that at least a portion of the first stream is passed to the contactor wherein it is contacted with the first effluent to produce said second effluent and a second stream comprising vaporised diluent and unreacted monomer.

The present invention has advantageously been found to result in transfer of components from the first stream into the feedstream for the second reactor. At the same time, components in the feedstream can be transferred into the first stream.

An example is entrained solids in the first stream. Entrained solids in the first stream are preferentially entrained into the stream to the reactor, and thereby are recycled to the reactor. Such solids can be catalytically active and their recycle to the reactor not only prevents the loss of such active components, but also prevents them being able to react and potentially cause fouling in downstream processing of the vapour. Filters and/or cyclones, which are often used to remove entrained fines from the vapour, for example of flash tank overhead lines, can be avoided.

The ability to avoid filters operating on the first stream is particularly advantageous. In particular, such filters can be prone to plugging due to condensation of components in the first stream at high pressure. Back-flushing of filters to remove blockages on high pressure filters can be generally harder and has greater propensity to cause filter damage. Thus, filters on high pressure streams can be particularly prone to operational problems.

Preferably, therefore, the present invention comprises no filters or solids removal equipment which act on the first stream, and in particular it is preferred that the first stream is passed from its source, for example a flash tank or other means to separate vaporised medium from the polymer solids/rest of the effluent, to the contacting step without passing through any filters. Further, the ability of the contacting step to remove entrained fines from the first stream prior to subsequent treatment of the first stream means that filters can be avoided in other parts of the high pressure recovery system. More generally therefore the polymerisation process preferably comprises no filters operating at pressures above 0.5 MPa, more preferably no filters operating above 0.4 MPa, and most preferably no filters operating above 0.2 MPa.

The present invention can also remove components from the effluent stream from a first reactor passed to a second reactor which are not required or are required in lesser amounts in the second reactor than in the first, and to enhance in the effluent stream passed to the second reactor components which are required or are required in greater amounts in the second reactor than in the first. In particular, it has been found that contacting of the separated vapour from the slurry exiting the second reactor, which can be inherently lower in the components not required or required in lesser amounts in the second reactor and higher in the components which are required or are required in higher amounts in the second reactor, results in a more favourable intermediate treatment.

In addition to solids, where present in the first stream, as noted above, the invention may be illustrated with respect to hydrogen and comonomer components. In some bimodal processes operating in two loop reactors in series, hydrogen may be desired in the first reactor but not in the second, or at least the amount of hydrogen desired in the second reactor is lower than in the first reactor. Similarly, comonomer may be desired in the second reactor but not in the first reactor, or at least the amount of comonomer required is higher in the second reactor than in the first reactor. Thus, the first polymer slurry and the first effluent also comprise hydrogen, and the second polymer slurry and the third effluent also comprise unreacted comonomer. In "conventional treatment", the first effluent may be passed to an intermediate treatment step in which at least a portion of the hydrogen is separated from the first effluent prior to its passage to the second reactor.

Whilst this can reduce the hydrogen significantly it can be difficult to remove sufficient hydrogen in this way without a significant reduction in pressure and/or without significant diluent or monomer loss with the hydrogen (which may be passed to flare).

In the process of the present invention it has been found that contacting of the first stream/separated vapour from the slurry exiting the second reactor, which has relatively reduced hydrogen and relatively increased comonomer compared to the feed stream/first effluent, results in an increase in the hydrogen in the second stream compared to the first stream and an increase in comonomer in the third stream/second effluent compared to the feed stream/first effluent.

The "increase" usually, and preferably, manifests itself as an increase in the absolute quantities of said components in said streams, measured in mass flow rates of the particular components.

The "increase" usually in addition manifests itself as increase in the ratios of the particular components to monomer in said streams, for example hydrogen to ethylene ratio and comonomer to ethylene ratio may be increased. In an alternative embodiment the increase may manifest itself only as an increase in the ratios of particular components to monomer i.e. without a requirement for an increase in the absolute mass flow rates. Thus, an increase in hydrogen is a particular stream means that the ratio of hydrogen to ethylene increases, whilst an increase in comonomer in a particular stream means that the ratio of comonomer to ethylene increases.

It will be apparent that in order to maintain a mass balance in the polymerisation system of the third aspect of the invention the majority of the diluent and unreacted monomers recovered from the third effluent actually have to be recycled to the first reactor rather than the second. By the process of the present invention the second stream, in an opposite result to the second effluent passing to the second reactor, is enhanced in the components desired in the first reactor and poorer in the components not desired, or desired in lesser quantities. Thus, in the example of hydrogen and comonomer given previously, the second stream is enhanced in hydrogen and poorer in comonomer than the first stream. This also therefore reduces the subsequent treatment of the vapour which is required prior to recycling to the first reactor.

More particularly, greater than 80%, such as greater than 90%, for example essentially all (by which is meant greater than 99%) of the comonomer in first stream prior to the contacting may be returned to second reactor via the feed-stream to the second reactor from the contacting.

In contrast, greater than 80%, such as greater than 90%, for example essentially all (by which is meant greater than 99%) of the hydrogen in the feed stream to the second reactor prior to the contacting is removed from the feed stream and passed to further processing.

For the above reasons, the present invention is particularly applicable to processes for producing bimodal polymer products. The separation step of the third aspect of the present invention is preferably a high pressure separation step, for example in a high pressure recovery system.

In a slurry polymerisation process the pressure and temperature in the high pressure recovery system are generally selected such that the majority of the diluent, monomer and comonomer are recovered in the vapour and can be condensed without compression for recycle to the reaction. Examples of such systems can be found, for example, in WO 2005/003188 which discloses the use of a higher pressure flash stage followed by a lower pressure flush stage. However, processes are also known where the lower pressure stage is a flash stage rather than a flush stage, or where both flashing and flushing occur in a single stage. (It can be noted that a flush stage can also be referred to as a "purge stage". The term "flush" is used herein for such steps to avoid any confusion with process purges, which are steps whereby streams are removed from a polymerisation process, for example to flare. The term "purge" as used herein therefore refers to a stream which is removed from the process rather than a flush step.)

The terms "high pressure" and "low pressure" are used herein to indicate relative pressures of different recovery systems.

Generally, however, "high pressure" as used herein generally refers to streams and stages which are at a pressure of 0.5 MPa (5 bar) and above, and usually 0.7 MPa (7 bar) and above, and "low pressure" generally refers to streams and stages which are at a pressure of less than 0.5 MPa (5 bar), usually less than 0.4 MPa (4 bar).

A low pressure recovery system, in contrast to the high pressure recovery system, leads to recovered components, such as diluent, monomer and comonomer, at lower pressures, and which generally need compression prior to recycle.

In a preferred embodiment the contacting of the first stream and the feed stream take place in a contactor which is configured in association with a fractionator to yet further enhance the separation achieved. In particular, the second stream recovered from the contactor is passed to a fractionator, from which heavier components, including comonomer, are recovered from the base and passed back to the contactor, whilst lighter components, such as hydrogen and monomer, and also diluent, are recovered from the fractionator as a vapour for further treatment and recycle.

Further, in a fourth aspect of the present invention there is provided a process for the polymerisation of monomer in a reactor, which process comprises contacting a first stream comprising vapour derived from the effluent withdrawn from the reactor with a feed stream to the reactor to produce a second stream comprising vapour which is passed to further processing and a third stream which is passed to the reactor, said contacting taking place by
   a. passing said first stream and said feed stream to a contactor,
   b. passing the second stream recovered from the contactor to a fractionator,
   c. recovering heavier components, including comonomer, from the base of the fractionator and passing said components back to the contactor,
   d. recovering lighter components from the fractionator as a vapour for further treatment and recycle.

The feed stream in this fourth aspect may be any stream comprising one or more components to be fed to the reactor. The feed stream is generally in a liquid form. Most preferably the feed stream in this fourth aspect comprises effluent derived from a previous reactor in series, in which case this fourth aspect is a preferred embodiment of the first and third aspects of the present invention.

For example, with respect to the third aspect of the present invention, the contactor and fractionator are configured such that:
   (i) slurry recovered from the contactor is recovered as the second effluent and passed to the second reactor,
   (ii) vapour recovered from the contactor is passed to the fractionator,
   (iii) liquid recovered from the fractionator is passed to the contactor, and
   (iv) vapour recovered from the fractionator is recovered.

More generally, the combined contactor/fractionator may be considered as a fractionation system which efficiently acts to fractionate the mixture of feed stream/first effluent and first stream initially passed to the contactor.

The vapour, or at least a portion thereof, recovered from the contactor or the contactor/fractionator combination is typically passed to one or more steps which may include removal of inert components, especially inert light components such as nitrogen and ethane which can otherwise build-up in the system, and/or which may include removal of "heavy" components, such as comonomer and components heavier than comonomer, prior to recycle.

After the high pressure separation step for separating a vapour comprising diluent and unreacted monomer from polymer solids the polymer solids are usually passed from the high pressure recovery system to a low pressure recovery system. The low pressure recovery system may comprise a low pressure separation step for separating further diluent, unreacted monomer and unreacted comonomer from said solids, and a recycle system for recycling at least a portion of the further diluent, unreacted monomer and unreacted comonomer.

The low pressure recovery system/recycle system may comprise a lights separator and/or a heavies separator for removing such components from the process.

By "lights separator" as used herein is meant a separator which is operated to provide separation of "lights" other than monomer, such as hydrogen and methane, from monomer and heavier compounds. As used herein "lights" means propane and molecules having a molecular weight less than propane.

By "heavies separator" as used herein is meant a separator which is operated to separate compounds heavier than the comonomer.

The general concept of "lights" and "heavies" separators for separation of such components in polymerisation processes is well-known. One example of such a system is taught by U.S. Pat. No. 6,292,191.

In a further aspect of the present invention it has surprisingly been found that hydrogen can be efficiently removed from the polymerisation system by treating two separate portions of the vapour stream recovered from the contactor at low temperature but at different pressures.

Thus, in a further aspect, the present invention provides a process for treatment of a first stream comprising vapour derived from the effluent withdrawn from a polymerisation reactor, which process comprises:
i) contacting said first stream with a feedstream to the reactor to produce a vapour comprising hydrogen,
ii) treating said vapour comprising hydrogen to produce and separate from each other a first liquid stream and a third stream comprising vapour,
iii) passing said third stream to a first separations step operating at greater than 0.5 MPa and at less than $-10°$ C. to separate hydrogen therefrom,
iv) passing a portion of the first liquid stream to a second separations step operating at less than 0.4 MPa and at less than $-10°$ C. to separate hydrogen therefrom.

The vapour comprising hydrogen may be the second stream previously described (where a contactor/fractionator combination is not present) or may be the vapour from a contactor/fractionator combination where such is used.

Steps (i), (ii) and (iii) are all performed at a pressure of at least 0.5 MPa, usually at least 0.7 MPa, and preferably of at least 0.8 MPa. Thus, said steps may all be considered part of the high pressure recovery system.

In contrast, step (iv) is operated at a relatively low pressure of less than 0.4 MPa, preferably less than 0.3 MPa, for example about 0.2 MPa. Preferably said step is integrated into the low pressure recovery system such that all of some of said portion of the first liquid stream may be recovered and recycled to the reactor.

The preferred features of first stream, the feedstream and the contacting of step (i) are as described previously. Thus, in the preferred embodiments the contacting of the first stream with the feedstream, which is preferably the effluent from a preceding reactor, results in an increase in hydrogen in the vapour comprising hydrogen compared to the first stream.

Step (ii) preferably comprises cooling the vapour to at least partially condense liquid therefrom, and separation of said third stream and first liquid stream. This cooling is preferably achieved using a cooling medium at above $0°$ C., most preferably using cooling water. By this step the majority of the diluent and unreacted monomers and comonomers are condensed, leaving mainly "lights" such as hydrogen and methane, although also some monomer, in the vapour phase.

The separation may be performed in any suitable vessel, for example a vapour/liquid separations drum.

In step (iii) said third stream is passed to a first separations step operating at greater than 0.5 MPa and at less than $-10°$ C. to separate hydrogen therefrom. Due to the cooling and separation in step (ii) the third vapour is only a relatively small portion of the vapour and thus a much lower volume of material need be cooled to the low temperature of this step.

The pressure in step (iii) is preferably approximately 0.8 MPa. The temperature in step (iii) is preferably less than $-20°$ C., more preferably less than $-30°$ C., and most preferably about $-35°$ C.

At such low temperatures hydrogen is efficiently separated from monomer and other components in the third vapour which can be recycled.

In step (iv) a portion of the first liquid stream is passed to a second separations step operating at less than 0.4 MPa and at less than $-10°$ C. to separate hydrogen therefrom.

It has been found that taken a portion of the first liquid stream, cooling and depressurising for a second separations step results in efficient further recovery of hydrogen from the process.

The portion of the first liquid stream which is cooled and depressurised for a second separations step usually comprises at least 10% by weight of the first liquid stream, preferably at least 20% by weight, such as between 20 and 40 wt % and most preferably 20 to 30 wt % of the first liquid stream.

The temperature in step (iv) is preferably less than $-20°$ C., more preferably less than $-30°$ C., and most preferably about $-35°$ C.

At such low temperatures hydrogen is again efficiently separated from monomer and other components in the portion of the first liquid stream. Remaining components of the stream can be recycled (after compression).

The present invention allows to obtain a polymerisation process which has a high efficiency for desired components of the final polymer, such as monomer, but "low" efficiency for other components (such as hydrogen).

As used herein, "efficiency" is a measure of the amount of a particular material which is fed and which is not purged from the process. For example, monomer efficiency is the amount of monomer fed which is not purged.

The monomer efficiency is a measure of the amount of the monomer which ends up in the polymer product, and is determined from the amount of fresh monomer fed to a process and the amount of monomer which is purged. The monomer purge rate may be determined from the purge flow and the concentration of monomer in the purge stream, which can be measured by GC, for each purge stream present. The efficiency may be determined instantaneously, based on flow rate measurements at a particular time, but preferably is determined over a period of time, for example based on averaged instantaneous measurements or on total amounts fed and purged determined over a period of at least several hours, as this generally gives a more accurate measurement. The monomer efficiency is determined by subtracting the amount purged from the amount fed, and then dividing the result by the amount fed. This answer is multiplied by 100 to give the efficiency as a percentage.

The process of the present invention is able to provide a monomer efficiency in excess of 99.5%, for example of 99.6% and above, and most preferably of 99.7% and above.

It is worth noting that, whilst monomer efficiencies of polymerisation processes are generally very high (above 99%), at the scale of commercial polymerisation processes even what appear as relatively minor increases in efficiency can result in significant cost savings, as well as significant reductions in hydrocarbon emissions or combustion products from hydrocarbon emissions (when flared). For example, in a process producing 50 tonnes/hour of polymer, an increase in monomer efficiency by only 0.1% is still a reduction in monomer losses of 50 kg/hour.

In contrast to a high monomer efficiency, it has been found that a low hydrogen efficiency of a polymerisation process can be advantageous. In particular, hydrogen is more cost effectively flared than recycled and recovered to the overall polymerisation process. An advantage of relatively low hydrogen efficiencies is that other impurities which can be present in fresh hydrogen feeds, such as methane and CO, are also efficiently purged from the system via the purge streams, and purification of fresh hydrogen feed via PSA can be avoided.

The present invention can result in a polymerisation process which preferably has a hydrogen efficiency, measured of the amount of the fed hydrogen which is not purged of 80% or less, preferably of 70% or less, and most preferably of 60% or less.

The hydrogen efficiency may be determined in a similar manner to the monomer efficiency, and in particular by determining the amount of hydrogen purged from the purge flow and the hydrogen concentration in the purge stream, which can be measured by GC, for each purge stream present and comparing this to the amount of hydrogen fed to the process.

EXAMPLE

Ethylene is polymerised in two slurry loop reactors in series to produce a bimodal polyethylene with a density of 948 kg/m$^3$ and a Melt Index ($MI_5$) of 0.31.

In the first reactor ethylene is polymerised in the substantial absence of comonomer, but in the presence of hydrogen and with isobutane as diluent. Polymer from the first reactor is passed to a second reactor wherein further ethylene is polymerised in the presence of 1-hexene as comonomer and the substantial absence of hydrogen, again in the presence of isobutane.

Polymer slurry is withdrawn from the first reactor and passed to a contacting vessel in the form of a stirred tank.

Polymer slurry is recovered from the base of the contacting vessel and passed to the second reactor.

Polymer slurry is withdrawn from the second reactor and passed via a slurry heater, in which the liquid components of the slurry are vaporised to a flash tank at a pressure of 0.85 MPa.

Polymer solids are withdrawn from the flash tank for further processing.

The vapour recovered from the flash tank is passed, without further treatment, as the first vapour to the contacting vessel where it is contacted with the slurry withdrawn from the first reactor. The contacting in the contacting vessel takes place at a pressure of 0.85 MPa.

Vapour is withdrawn from the top of the contacting vessel (second vapour) and passed to a fractionator in which it is contacted with a reflux stream. Vapour recovered overhead is cooled and condensed. A portion is utilised as the reflux stream to the fractionator. The majority of the remainder is cycled to the first reactor.

Liquids recovered from the base of the fractionator are returned to the contacting vessel.

The combined "contacting vessel/fractionator" is herein referred to as a "fractionation system".

The first vapour is passed to the contacting vessel. The stream comprises predominantly isobutane, but also approximately 2700 kg/hr of 1-hexene and smaller quantities of hexane, ethane, ethylene and hydrogen.

The slurry from the first reactor is also passed to the contacting vessel. The slurry liquid comprises predominantly isobutane with smaller quantities of ethane and ethylene. The stream is substantially free of 1-hexene but comprises approximately 13 kg/h of hydrogen.

The vapour recovered from the contacting vessel (second vapour stream) is substantially reduced in 1-hexene and hexane flow compared to the first vapour stream, but comprises substantially all of the hydrogen fed to the contacting vessel.

The vapour from the contacting vessel is passed to the fractionator in which further separation occurs. The liquid recovered from the base and recycled to the contacting vessel comprises essentially all of the 1-hexene and hexane in the second vapour stream. The vapour recovered from the fractionator is substantially free of 1-hexene and hexane, but comprises substantially all of the hydrogen fed to the fractionator, corresponding to 99.5% of all hydrogen fed to the fractionation system in total).

The slurry recovered from the contacting vessel is, in contrast, substantially free of hydrogen, but comprises essentially all of the 1-hexene and hexane fed to the fractionation system.

It can be seen that the contacting vessel efficiently separates hydrogen from the slurry from the first reactor into the second vapour stream (the majority of which is cycled to the first reactor, where hydrogen is desired), thereby also removing it from the second slurry (which is subsequently passed to the second reactor where hydrogen is not desired). At the same time 1-hexene is separated from the vapour stream in the contacting vessel.

Further, by use of a fractionator in combination with the contacting vessel 1-hexene is essentially completely separated from the first vapour stream and into the second liquid (which is cycled to the second reactor, where the 1-hexene is required.)

Other "light" components, such as nitrogen, methane, ethane, ethylene and propane are also preferentially separated into the vapour stream exiting the fractionation system. In particular, approximately 99% of nitrogen, 98% of methane, 95% of each of ethane and ethylene, and 85% of propane end up in the vapour stream exiting the fractionation system (compared to "total" of each component fed to the fractionation system).

This stream is cooled to 35° C. (at 0.8 MPa) and passed to a liquid/vapour separation drum. Approximately 3500 kg/h of vapour is recovered and further cooled to −35° C. (still at 0.8 MPa) to separate a stream comprising 12 kg/h of hydrogen, which is flared. This stream also comprises methane, nitrogen, ethane and propane.

The majority of the liquid from the liquid/vapour separation drum is recycled to the first reactor. A portion of the liquid from the liquid vapour separation drum, comprising principally isobutane, but also quantities of ethylene, ethane, propane and other components, including approximately 0.5 kg/h of hydrogen, is however cooled to −35° C. and let-down in pressure to 0.2 MPa in the low pressure separations system. From the low pressure separations system there is separated and passed to flare a stream comprising 0.5 kg/h of hydrogen. Although this stream comprises quantities of isobutane, methane, nitrogen, ethane and propane, the majority (99.5 wt %) of the isobutane in the stream passed to the low pressure separations step is recovered for recycle (after compression) rather than flared.

The invention claimed is:

1. A process for the polymerisation of monomer in at least first and second reactors operated in series, which process comprises either:
 (i) contacting a first stream comprising vapour derived from the effluent withdrawn from the second reactor with a feed stream to the second reactor, said feed stream comprising effluent derived from the first reactor and said first stream having been separated from the polymer withdrawn from the second reactor at a pressure of 0.5 MPa (5 bar) or above, or
  (ii) contacting a first stream comprising vapour derived from the effluent withdrawn from a subsequent reactor with a feed stream to the second reactor, said feed stream comprising effluent derived from the first reactor.

2. A process according to claim 1 which comprises first and second slurry loop polymerisation reactors connected in series.

3. A process according to claim 1 wherein the feed stream is a slurry of polymer solids in a liquid medium from a first slurry loop polymerisation reactor.

4. A process according to claim 1 wherein the effluent withdrawn from the second reactor is a slurry of polymer solids in a liquid medium comprising diluent, and wherein the first stream is derived from the effluent by flashing all or a portion of the liquid medium to form a vapour, and separating this from the polymer solids.

5. A process according to claim 4 wherein said first stream comprises a majority of the vaporised components of the liquid medium in the effluent withdrawn from the second reactor and at least 80% by weight of the first stream is in vapour form when brought into contact with the feed stream.

6. A process according to claim 1 wherein the first stream is brought into contact with the feedstream to the second reactor at a pressure of 0.5 MPa (5 bar) or above.

7. A process according to claim 1 wherein the first stream is passed from its source to the contacting step without any compression and/or wherein the first stream is passed from its source to the contacting step without passing through any filters.

8. A process according to claim 1 wherein the first stream has been separated from the polymer withdrawn from the subsequent reactor at a pressure of 0.5 MPa (5 bar) or above.

9. A process according to claim 1 which is a process for the polymerisation of monomer in two slurry loop reactors connected in series, which process comprises:
  1) Polymerising in a first loop reactor, monomer in the presence of a diluent to produce a first polymer slurry comprising polymer solids suspended in a liquid medium comprising diluent and unreacted monomer,
  2) Withdrawing a portion of the first polymer slurry as a first effluent comprising solid polymer, diluent and unreacted monomer, and passing said first effluent to a contactor to form a second effluent comprising solid polymer, diluent and unreacted monomer,
  3) Passing said second effluent to a second loop reactor,
  4) Polymerising in the second loop reactor, monomer in the presence of said second effluent, to produce a second polymer slurry comprising polymer solids suspended in a liquid medium comprising diluent and unreacted monomer,
  5) Withdrawing a portion of the second polymer slurry as a third effluent comprising solid polymer, diluent and unreacted monomer, and
  6) Passing said third effluent to a separation step for separating a first stream comprising vaporised diluent and unreacted monomer from said polymer solids, said separation step being a high pressure separation step at a pressure of 0.5 MPa (5 bar) or above,
  characterised in that at least a portion of the first stream is passed to the contactor wherein it is contacted with the first effluent to produce said second effluent and a second stream comprising vaporised diluent and unreacted monomer.

10. A process according to claim 9 wherein the first stream comprises entrained solids which are preferentially entrained into the second effluent.

11. A process according to claim 9 wherein the first polymer slurry and the first effluent also comprise hydrogen, and the second polymer slurry and the third effluent also comprise unreacted comonomer, and wherein the contacting of the first stream and first effluent results in an increase in the hydrogen in the second stream compared to the first stream and an increase in comonomer in the second effluent compared to the first effluent.

12. A process according to claim 9 wherein the second stream is enhanced in hydrogen and poorer in comonomer than the first stream.

13. A process according to claim 9 wherein the contacting takes place in a contactor which is configured in association with a fractionator such that the second stream recovered from the contactor is passed directly to a fractionator, from which heavier components, including comonomer, are recovered and passed directly back to the contactor, whilst lighter components are recovered from the fractionator as a vapour for further treatment and recycle.

14. A process according to claim 9 wherein the separation step is in a high pressure recovery system and polymer solids are passed from the high pressure recovery system to a low pressure recovery system which comprises a low pressure separation step for separating further diluent, unreacted monomer and unreacted comonomer from said solids, and a recycle system for recycling at least a portion of the further diluent, unreacted monomer and unreacted comonomer.

15. A process according to claim 14 wherein the low pressure recovery system/recycle system comprises a lights separator and/or a heavies separator for removing such components from the process.

16. A process for treatment of a first stream comprising vapour derived from the effluent withdrawn from a polymerisation reactor, which process comprises:
  i) contacting said first stream with a feed stream to the reactor to produce a vapour comprising hydrogen,
  ii) treating said vapour comprising hydrogen to produce and separate from each other a first liquid stream and a third stream comprising vapour,
  iii) passing said third stream to a first separations step operating at greater than 0.5 MPa and at less than −10° C. to separate hydrogen therefrom, each of steps (i), (ii) and (iii) being performed at a pressure of at least 0.5 MPa, and
  iv) passing a portion of the first liquid stream to a second separations step operating at less than 0.4 MPa and at less than −10° C. to separate hydrogen therefrom.

* * * * *